United States Patent
Sellers et al.

(10) Patent No.: US 6,651,665 B1
(45) Date of Patent: Nov. 25, 2003

(54) ROTATING MAGNETIC GUIDE INTUBATION SYSTEM

(75) Inventors: D. Matthew Sellers, Knoxville, TN (US); Ivan N. Cooper, Knoxville, TN (US); Bruce L. Fariss, Knoxville, TN (US)

(73) Assignee: Ibionics, Inc., Knoxville, TN (US)

( * ) Notice: Subject to any disclaimer, the term of this patent is extended or adjusted under 35 U.S.C. 154(b) by 74 days.

(21) Appl. No.: 10/078,133

(22) Filed: Feb. 19, 2002

(51) Int. Cl.⁷ ................................................ A62B 9/06
(52) U.S. Cl. ................................................ 128/207.14
(58) Field of Search ...................... 128/200.26, 207.14, 128/207.15, 207.29

(56) References Cited

U.S. PATENT DOCUMENTS

| | | | | |
|---|---|---|---|---|
| 2,463,149 A | * | 3/1949 | Caine | 128/200.26 |
| 2,541,402 A | * | 2/1951 | Caine | 128/200.26 |
| 2,862,498 A | * | 12/1958 | Weekes | 128/207.14 |
| 3,314,431 A | * | 4/1967 | Smith, Jr. | 128/200.26 |
| 3,674,014 A | | 7/1972 | Tillander | |
| 3,996,939 A | * | 12/1976 | Sheridan et al. | 128/207.14 |
| 4,170,232 A | * | 10/1979 | Khoury | 600/581 |
| 4,244,362 A | * | 1/1981 | Anderson | 128/200.26 |
| 4,431,005 A | * | 2/1984 | McCormick | 600/433 |
| 4,444,185 A | * | 4/1984 | Shugar | 128/207.29 |
| 4,445,501 A | * | 5/1984 | Bresler | 600/12 |
| 4,567,882 A | * | 2/1986 | Heller | 600/249 |
| 4,593,687 A | * | 6/1986 | Gray | 128/200.26 |
| 4,865,586 A | * | 9/1989 | Hedberg | 604/93.01 |
| 4,913,139 A | | 4/1990 | Ballew | |
| 4,943,770 A | * | 7/1990 | Ashley-Rollman et al. | 324/207.17 |
| 5,235,970 A | * | 8/1993 | Augustine | 128/200.26 |
| 5,257,636 A | * | 11/1993 | White | 128/897 |
| 5,390,661 A | | 2/1995 | Griffith et al. | |
| 5,429,131 A | | 7/1995 | Scheinman et al. | |
| 5,560,351 A | * | 10/1996 | Gravenstein et al. | 128/200.26 |
| 5,775,322 A | | 7/1998 | Silverstein et al. | |
| 5,785,051 A | * | 7/1998 | Lipscher et al. | 128/207.15 |
| 5,996,582 A | * | 12/1999 | Turnbull | 128/207.29 |
| 6,013,038 A | | 1/2000 | Pflueger | |
| 6,157,853 A | | 12/2000 | Blume et al. | |
| 6,161,537 A | * | 12/2000 | Gravenstein et al. | 128/200.26 |
| 6,173,199 B1 | | 1/2001 | Gabriel | |
| 6,296,630 B1 | | 10/2001 | Altman et al. | |
| 6,349,720 B1 | * | 2/2002 | Clark | 128/200.26 |
| 6,553,993 B2 | * | 4/2003 | Toti et al. | 128/207.14 |

* cited by examiner

*Primary Examiner*—Aaron J. Lewis
(74) *Attorney, Agent, or Firm*—Pitts & Brittian, P.C.

(57) ABSTRACT

A magnetic guide system for intubation of a tube into a patient's passageway. The system includes an intubation tube having a distal end sized for insertion into the patient. The tube includes a proximal end maintained external of the patient, and a flexible mid-portion allow lateral bending. A magnet member is enclosed on the distal end by a means for containment to allow rotation of the magnet member therein. The means for containment is composed of a material for passage of gases and liquids therethrough, while the magnet member is rotatable therein. The distal end and enclosed magnet member is insertable into a patient's passageway. Movement of the intubation tube distal end and rotating magnet member is influenced by movement of an external magnetic field from at least one magnet positioned external of the patient. A method for intubation of the intubation tube into a patient's passageway leading to a target organ is also disclosed.

13 Claims, 4 Drawing Sheets

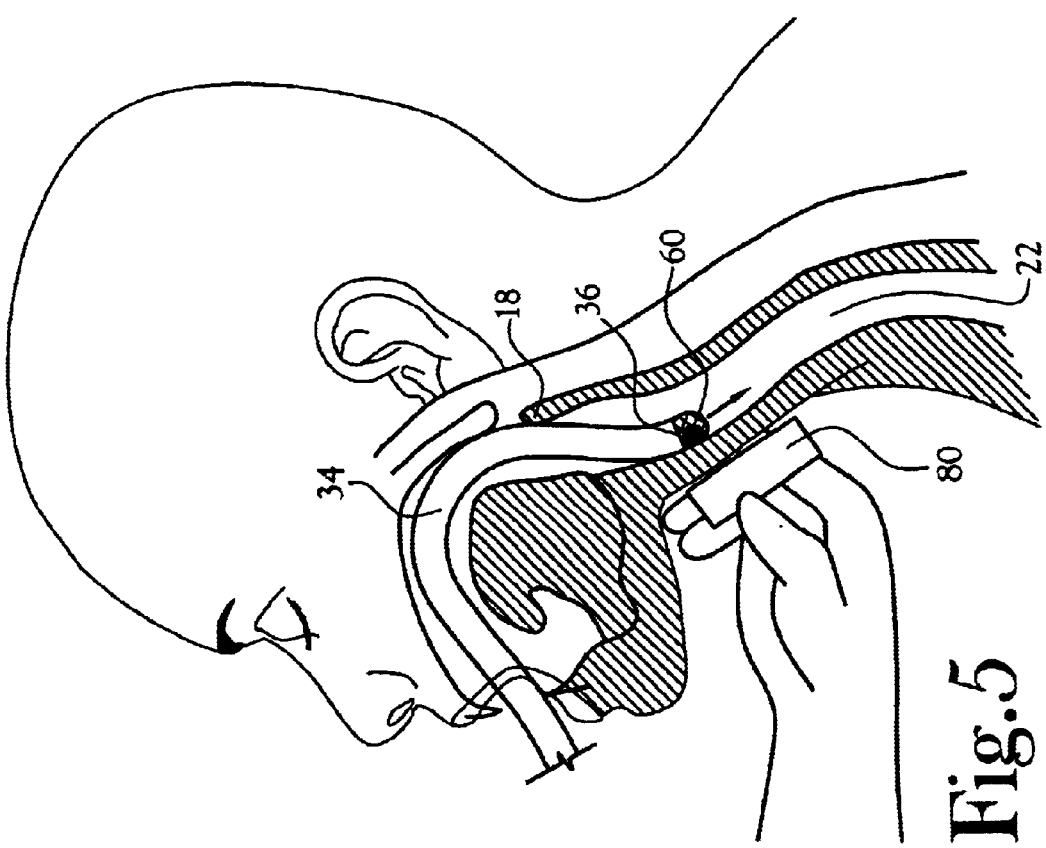

ROTATING MAGNETIC GUIDE INTUBATION SYSTEM

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of Invention

This invention pertains to intubation devices for insertion of a tube into a patient. More particularly, this invention pertains to an intubation system utilizing an intubation device having a rotating magnetic member that is guided through a patient's target passageway by an external magnetic field.

2. Description of the Related Art

Prior intubation devices have provided various guide mechanisms to direct a tube into an organ of a patient such as through the larynx, trachea, nose, or through the abdominal wall. Typical prior intubation device include insertion of a guide device such as a guide wire, insertion sheath, and/or guide cylinder, that is inserted into the appropriate body opening. A tube is connected to the guide wire or inserted through the sheath or cylinder for intubation. The intubation process typically includes an attendant manipulating a guide wire or tube into the appropriate passageway by rotating, wiggling, turning, and extending and periodically retracting the guide device until the tube is inserted into the appropriate organ. Many attendants are trained to utilize a laryngoscope that allows visualization of the glottis and trachea. The intubation process is often attempted by trained attendants and is typically a time-critical process of insertion of an endotracheal tube to provide an unobstructed airway into a patient's trachea. Guiding the endotracheal tube into a trachea includes threading the tube into the glottic opening and past the vocal chords, which is a difficult procedure for trained emergency response personnel who may not practice the procedure often. If the procedure is not completed quickly and properly, the patient may suffer brain injury due to lack of oxygen from partially blocked breathing passageways. Any delay in placement of an endotracheal tube may delay performance of additional life-saving procedures on a patient.

There is a need for a system for positioning an intubation tube without requiring visualization of passage of the tube into appropriate passageways of a patient. A further need includes a magnetic guide intubation system that allows insertion of an intubation tube into appropriate passageways of a patient without twisting or turning of the external end of the tube. An additional need includes a magnetic guide intubation system that does not require insertion of additional internal guide wires or channels attached to the tube.

BRIEF SUMMARY OF THE INVENTION

According to one embodiment of the present invention, a rotating magnetic guide intubation system is disclosed along with a method of operation, for rapid intubation into a patient's pharynx leading to a target organ of a patient. The rotating magnetic guide intubation system includes a length of an intubation tube having a magnet member positioned at a distal end of the tube. The magnet member includes a magnetic sphere enclosed within a means for containment positioned at the tube distal end. The magnetic sphere is freely rotatable within the means for containment. The means for containment includes an enclosure that maintains its shape while containing the magnetic sphere therein, when the tube distal end is inserted into a pathway into the patient. The enclosure does not occlude an end opening of the distal end of the tube, therefore air may pass through the tube distal end without impacting the movement or positioning of the magnetic sphere. As the distal end of the tube is inserted into the patient, the rotating magnetic guide is influenced a magnetic field from at least one magnet positioned external of the patient. An operator can remotely adjust the position and orientation of the distal end of the tube during intubation into a patient's pathway without insertion of a visualization device, a guide wire or a guide channel.

A method of operation for rapid intubation of a patient includes the step of providing an intubation tube including a rotating magnet member on a distal end of the tube, with the magnetic member enclosed on the tube distal end by a means for enclosure. A step of intubating includes inserting the distal end of the tube into a passageway of the patient, with the distal end having the rotating magnetic guide thereon. A step of positioning includes remotely adjusting the path of the distal end of the tube by positioning at least one external magnet proximal to the patient's dermal surface, and remotely adjusting the path of the tube distal end into the patient's passageway. A step of manipulating includes moving the at least one external magnet along a path proximal to the patient's dermal surface. A step of inserting includes inserting a selected length of the intubation tube into the patient's passageway, with the distal end having the rotating magnet member thereon guided toward a target organ within the patient.

BRIEF DESCRIPTION OF THE SEVERAL VIEWS OF THE DRAWINGS

The above-mentioned features of the invention will become more clearly understood from the following detailed description of the invention read together with the drawings in which:

FIG. 5 is a perspective side view of a step of positioning the rotating magnetic guide into a trachea of a patient.

DETAILED DESCRIPTION OF THE INVENTION

Figure 1:
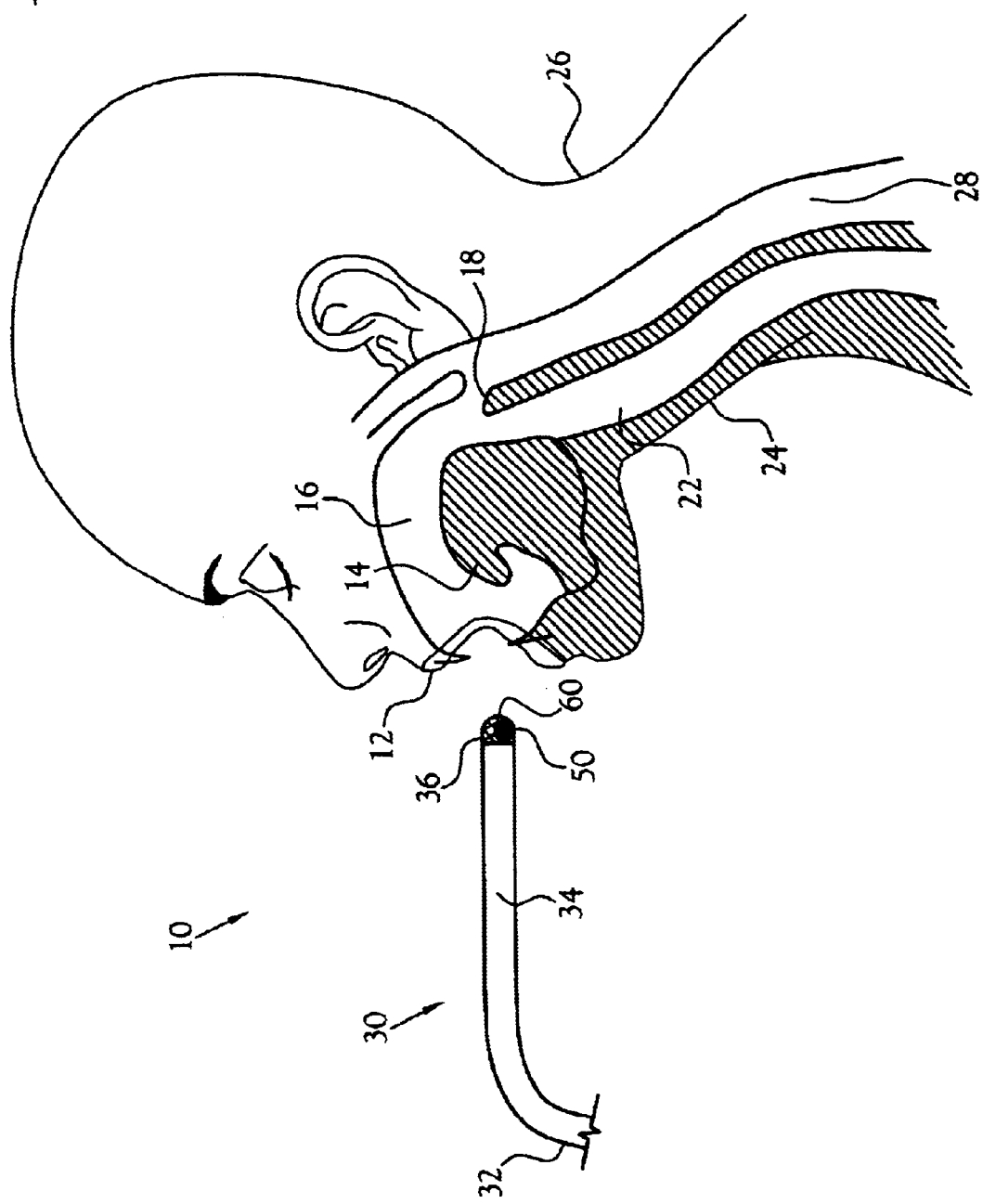
FIG. 1 is a side perspective view of a rotating magnetic guide for intubation of the present invention, positioned for insertion into a patient's mouth.
Figure 4:
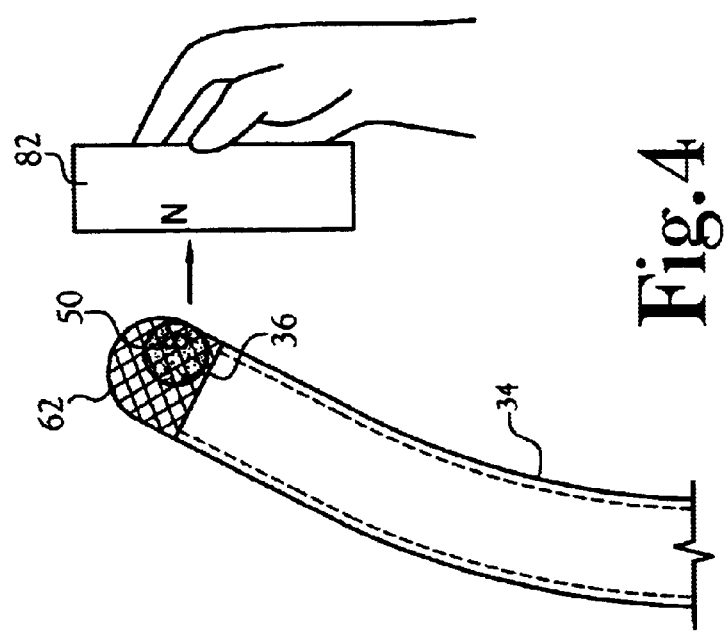
FIG. 4 is a side view of the rotating magnetic guide of FIG. 2, attracted in a second lateral direction toward a hand-held magnet.
Figure 3:
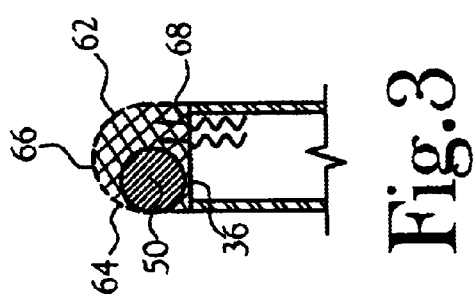
FIG. 3 is a section along 3—3 of FIG. 2, illustrating the interior and cross-section of the means for enclosure having a magnet therein.
Figure 2:
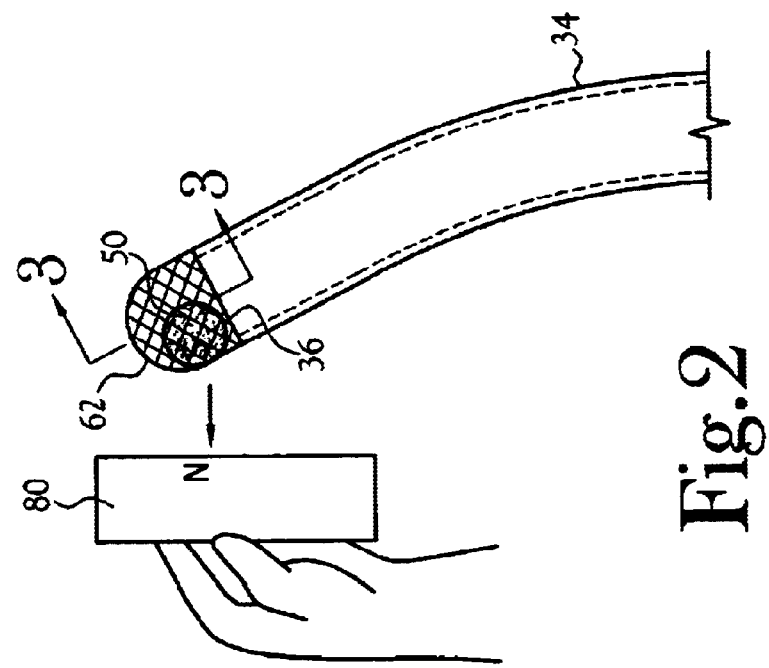
FIG. 2 is a side view of the rotating magnetic guide of FIG. 1, attracted in a first lateral direction toward a hand-held magnet.
Figure 6:
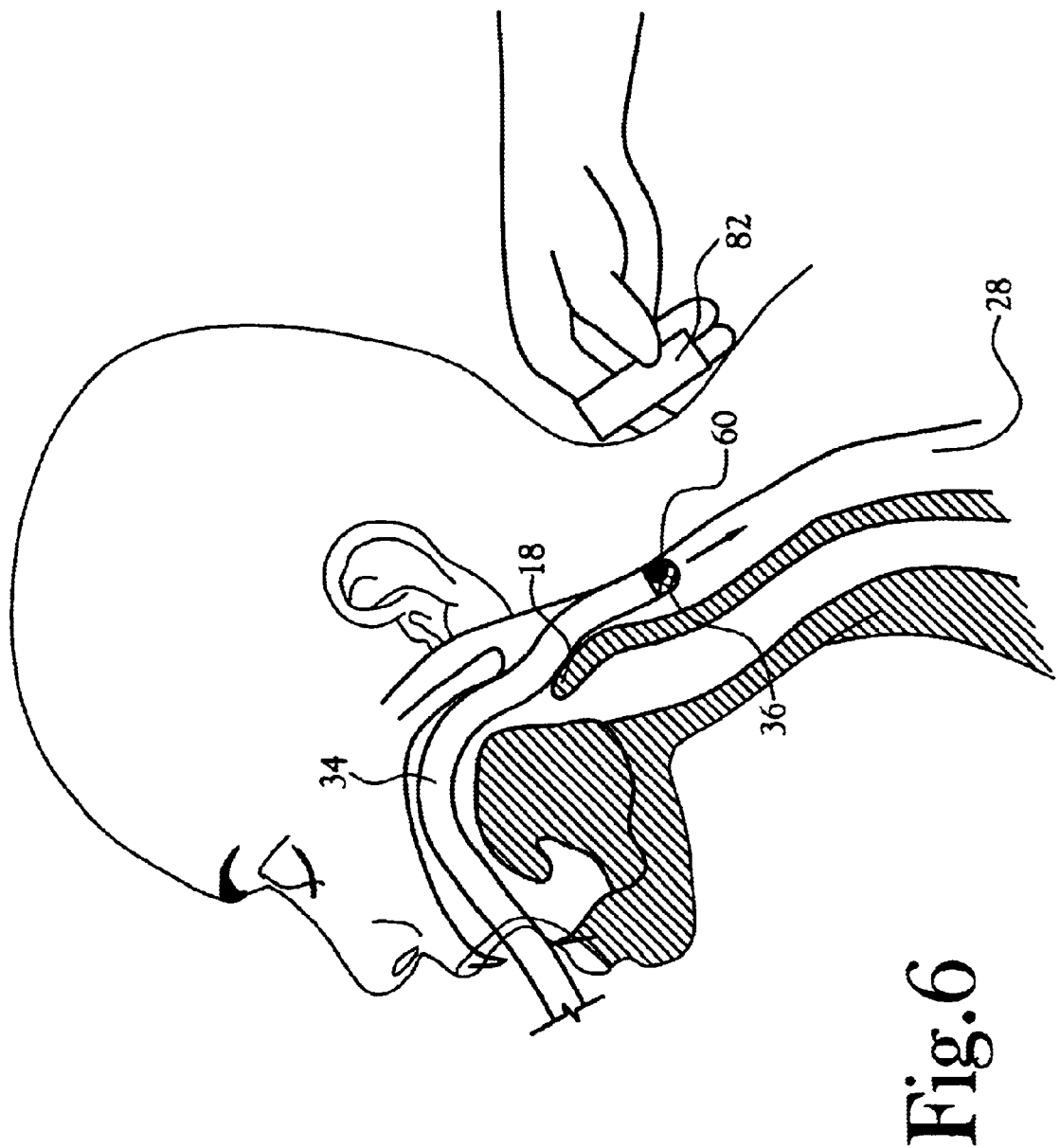
FIG. 6 is a perspective side view of a step of positioning the rotating magnetic guide into an esophagus of a patient.

A rotating magnetic guide system 10 is disclosed along with a method of operation for a rapid intubation procedure by a properly trained person for insertion of a substantially hollow intubation tube 30 into a patient's mouth 12 (see FIG. 1), past the tongue 14, into the oral cavity 16, and past the glottic opening 18 and vocal cords for passage into the trachea 22 or esophagus 28 of a patient. The magnetic guide 10 includes a length of an intubation tube 30 having side walls that are bendable in a lateral dimension along the axial length of the tube 30. The intubation tube 30 includes a first end 32 proximal to, and held by the properly trained person, a flexible mid-portion 34, and a distal end 36 having a rotating magnet 50 positioned within a means for enclosure 60 attachable on the distal end 36 of the intubation tube 30 (see FIGS. 2 and 3). The rotating magnet 50 includes a generally spherical magnet that is freely rotatable within the means for enclosure 60. The magnet 50 is typical of magnets known to those skilled in the art, having a north orienting portion and a south orienting portion. The magnet 50 may have any outer surface encased in a coating, or may have an enclosure such as a shell or a similar encasing layer. The materials utilized for the coating or shell are maintained in a sterilized condition, or are quickly sterilized before the intubation procedure is initiated.

The means for enclosure 60 includes a containment shell 62 that is atttachable on the tube distal end 36. The containment shell 62 includes a generally cylindrical side wall 64, distal end portion 66, and base end portion 68 (see FIG. 3). The base end portion 68 is firmly attachable to the open, hollow distal end 36 of the intubation tube 30. The side wall 64, distal end portion 66 and base end portion 68 are composed of a wire mesh material, or a similar material that includes at least one surface that is substantially porous to the passage of air and liquids, such as a basket or a hollow sphere, and that encloses the freely rotatable magnet 50. The rotating magnet 50 is freely rotatable within the containment shell 62. The means for enclosure 60 includes a plurality of pores to allow free passage of air and/or gases such as pure oxygen into and out of the patient during normal inhalation and exhalation by the patient. The means for enclosure 60 is intended to maintain an spherical or semispherical shape during the intubation procedure without collapsing on the rotating magnet 50 therein. The means for enclosure 60 does not occlude an end opening of the distal end 36 of the tube 30, therefore air or liquids may pass through the tube distal end without impacting the movement or positioning of the magnetic sphere. As the distal end 36 of the intubation tube 30 is inserted into the patient, the rotating magnetic guide 10 is influenced by one or more external magnets 80, 82 (see FIGS. 2, 4, 5 and 6) positioned proximal to external dermal surfaces 24, 26 of the patient, therefore an operator can remotely adjust the position and orientation of the distal end of the tube during intubation into the trachea 22 or the esophagus 28 without insertion of a visualization device such as a mirror, or a guide wire and/or a guide tube.

An alternative embodiment includes an intubation tube 30 having a rotating magnet 50 that is freely rotatable within a containment shell 62 of a means for containment of the rotating magnet 50 and for enclosure 60 of the tube distal end 36. The means for containment and enclosure 60 may include a spherical or a hemispherical shell 62 composed of a wire mesh material that allows unhindered movement of air or liquids through the tube distal end 36, without allowing the escape of the rotating magnet 50. The rotating magnet 50 is sized to have a diameter smaller than about 70% to about 80% of the length between the porous side walls 64, distal end 66, and base end 68 of the spherical or hemispherical shell, to prevent blockage of the porous base end 68 attached to the distal end 36 of the hollow tube 30. The spherical or hemispherical shell 62 is firmly connected to the distal end 36 of the intubation tube 30 to minimize the disassembly of the components of the spherical or hemispherical shell 62 during insertion within the patient. The porous shell 64, 66 is substantially rigid to maintain its shape during the insertion of the distal end 36 past the glottic opening 18 and into the trachea 22 during the intubation procedure. An alternative embodiment includes at least one magnet positioned on the distal end, with the at least one magnet including two substantially spherical magnets (not shown), that are independently rotated within the spherical or hemispherical shell 62 when the distal end 66 is in the presence of a magnetic field positioned external of the patient. An additional embodiment includes an endotracheal inflatable cuff (not shown) that is connected to the intubation tube 30 at about a mid-portion 34 of the tube, with the inflatable cuff surrounding the outer diameter of the mid-portion 34. The inflatable cuff is inflated after the tube 30 is inserted in the trachea 22 by the rotating magnet 50 influenced by manipulation of external magnets 80, 82. When the inflatable cuff is fully inflated, the endotracheal inflatable cuff prevents aspiration of foreign materials into the bronchi of the patient.

A method of operation for rapid intubation of an intubation tube by a properly trained person includes the step of providing an intubation tube 30 having a distal end 36 and a flexible mid-portion 34 having bendable side walls that are bendable in a lateral dimension along the axial length of the intubation tube 30. A step of enclosing includes positioning a generally spherical magnet member 50 within a means for enclosure 60 having a spherical or hemispherical shell 62 such that the magnet member 50 is freely rotating within the shell 62. A step of intubating includes inserting the tube distal end into at least one passageway within the patient, with the distal end having the rotating magnetic guide thereon. A step of positioning includes remotely adjusting the path of the distal end of the tube by applying and positioning at least one external magnet 80 proximal to the dermal surface of the patient's throat and neck to the passageway. The step of positioning remotely adjusts the position of the intubation tube 30 for insertion into the trachea 22. A step of repositioning may be included to provide a step of moving the at least one external magnet 80 along a path on the patient's external dermal surface (see FIG. 5), therefore remotely positioning the magnet member 50 and distal end 36 into and into the trachea 22 for positioning proximal to the target organ of the lungs. A further step includes manipulating at least one second external magnet 82 along a second path on the patient's external dermal surface of the back of the neck (see FIG. 6), therefore influencing the position of the rotating magnet member 50 and the distal end 36 of the intubation tube 30 into and into the esophagus 28 for positioning proximal the target organ of the stomach. A further step includes inserting the proximal end 32 up to the mouth 12 of the patient, with the length of the intubation tube 30 inserted into the trachea 22 or the esophagus 28 toward the target organ in the patient.

From the foregoing description, it will be recognized by those skilled in the art that the rotating magnetic guide system 10 utilizing an intubation tube having the rotating magnet member provides a system for positioning the intubation tube without requiring visualization of passage of the intubation tube into appropriate passageways of a patient. A further benefit includes a rotating magnet guide system for intubation without twisting or forced turning of a tube during insertion past the glottic opening for insertion into an appropriate passageway of a patient. An additional benefit includes a rotating magnet guide system for insertion of an intubation tube without insertion of additional internal guide channels or guide wires during placement of the intubation tube into an appropriate passageway of a patient.

While the present invention has been illustrated by description of several embodiments and while the illustrative embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

Having thus described the aforementioned invention, we claim:

1. A magnetic guide system for intubation of a tube into a passageway of a patient, comprising:
    a tube having a distal end sized for intubation into a patient, said tube having a proximal end maintained exterior of the patient, said tube having a flexible mid-portion;
    a magnet member positioned on said tube distal end; and
    a means for containment for said magnet member, said means for containment encloses said magnet member with sufficient space for rotation of said magnet member therein, said means for containment is composed of a material for passage of gases and liquids therethrough while said magnet member is retained therein;
    whereby said tube distal end having said magnet member thereon is inserted into the passageway of the patient, said magnet member rotates freely within said means for containment when in the presence of a magnetic field positioned external of the patient during intubation of said tube distal end into a passageway of the patient.

2. The magnetic guide system of claim 1 wherein said magnet member includes a substantially spherical magnet enclosed within said means for containment, said substantially spherical magnet is rotatable when in the presence of the magnetic field positioned external of the patient and said means for containment is displaced toward the magnetic field positioned external of the patient, whereby said tube distal end is displaced toward the magnetic field as said tube distal end is guided into the passageway of the patient by the attendant.

3. The magnetic guide system of claim 2 wherein said means for containment includes a generally hemispherical shell of a substantially porous material for passage of gases and liquids therethrough, said substantially spherical magnet is sized to fit within said generally hemispherical shell to allow unhindered movement of air or liquids through said tube distal end and past said substantially spherical magnet within said generally hemispherical shell.

4. The magnetic guide system of claim 1 wherein said flexible mid-portion of said tube includes a cylindrical configuration having bendable walls for lateral bending of said mid-portion in a lateral dimension along the axial length of the tube.

5. The magnetic guide system of claim 1 wherein a magnetic field positioned external of the patient includes at least one external magnet positioned against a dermal surface of the patient proximal to the passageway inside the patient, said at least one external magnet is manipulated along the dermal surface proximal to the passageway of the patient into which said tube distal end is inserted.

6. The magnetic guide system of claim 5 wherein a magnetic field positioned external of the patient further includes at least one second external magnet positioned against a second location on the dermal surface of the patient proximal to the passageway inside the patient, said at least one second external magnet is manipulated along the second location on the dermal surface proximal to the passageway of the patient into which said tube distal end is inserted.

7. A magnetic intubation guide for insertion of a tube into a passageway of a patient, comprising:
    a tube having a distal end sized for intubation into a patient, said tube having a proximal end maintained exterior of the patient, said tube having a flexible mid-portion;
    a magnet member positioned on said distal end of said tube, said magnet member includes at least one magnet positioned on said tube distal end, said at least one magnet is rotatable when in the presence of a magnetic field positioned external of the patient; and
    a means for containment for said at least one magnet member, said means for containment encloses said at least one magnet member with sufficient space for rotation of said at least one magnet member therein, said means for containment is composed of a substantially porous material for passage of gases and liquids therethrough while said at least one magnet member is retained therein;
    whereby said tube distal end having said at least one magnet member thereon is inserted into the passageway of the patient, said at least one magnet member is rotatable freely within said means for containment when in the presence of the magnetic field positioned external of the patient during intubation of said tube distal end into a passageway of the patient.

8. The magnetic intubation guide of claim 7 wherein said means for containment includes a generally hemispherical shell composed of said substantially porous material, said substantially spherical magnet is sized to fit within said generally hemispherical shell to allow unhindered movement of air or liquids through said tube distal end and past said substantially spherical magnet within said generally hemispherical shell.

9. The magnetic intubation guide of claim 8 wherein said flexible mid-portion of said tube includes a cylindrical configuration having bendable walls for lateral bending of said mid-portion in a lateral dimension along the axial length of the tube.

10. The magnetic intubation guide of claim 9 wherein a magnetic field positioned external of the patient includes at least one external magnet positioned against a dermal surface of the patient proximal to the passageway inside the patient, said at least one external magnet is manipulated along the dermal surface proximal to the passageway of the patient into which said tube distal end is inserted.

11. The magnetic intubation guide of claim 10 wherein a magnetic field positioned external of the patient further includes at least one second external magnet positioned against a second location on the dermal surface of the patient proximal to the passageway inside the patient, said at least one second external magnet is manipulated along the second location on the dermal surface proximal to the passageway of the patient into which said tube distal end is inserted.

12. A method for intubation of a magnetic guide tube into a passageway and toward a target organ of a patient, comprising the steps of:
    providing an intubation tube having a distal end having a magnet member positioned in a rotating configuration thereon;

intubating said intubation tube into a passageway of the patient;

positioning said intubation tube within the passageway of the patient by adjusting the path into the passageway of said distal end of said intubation tube by placing at least one external magnet proximal to a dermal surface of the patient, said step of positioning remotely adjusting the path into the passageway;

manipulating said at least one external magnet along the dermal surface of the patient for influencing the position of said distal end of said intubation tube within the passageway; and inserting a selected length of said intubation tube into the passageway with said distal end of said intubation tube positioned toward a target organ within the patient.

13. The method for intubation of claim 12 wherein said step of providing includes a step of enclosing said magnet member within a means for enclosure positioned on said distal end of said intubation tube, said step of enclosing providing at least one rotating magnet member within said means for enclosure, said means for enclosure having porous walls and end surfaces allowing air to pass therethrough.

* * * * *